(12) United States Patent
Goldstein et al.

(10) Patent No.: US 6,329,412 B1
(45) Date of Patent: Dec. 11, 2001

(54) BISAMIDINE COMPOUNDS AS ANTIPROLIFERATIVE AGENTS

(75) Inventors: Steven W. Goldstein, Noank; Banauara L. Mylari, Waterford; Jose R. Perez, Salem; Edward A. Glazer, Waterford, all of CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/535,359

(22) Filed: Mar. 24, 2000

Related U.S. Application Data

(60) Provisional application No. 60/064,198, filed on Nov. 4, 1997.
(51) Int. Cl.[7] ................ A61K 31/415; A61K 31/405
(52) U.S. Cl. ................... 514/385; 514/394; 514/415
(58) Field of Search .................... 514/415, 394, 514/385

(56) References Cited
PUBLICATIONS

De Clercq et al., J. Med. Chem., (1980), 23(7), 787–795.*
Bestor, et al., Proc. Nat. Acad. Sci., 80, pp. 5559–5563 (1983).
Li, et al., Cell, 69, pp. 915–926 (1992).
Shen, et al., Cell, 71, pp. 1073–1080 (1992).
Laird, et al., Cell, 81, pp. 197–205 (1995).
Schroeder, et al., Biochem. & Biophys. Res. Comm., 235, pp. 403–406 (1997).

* cited by examiner

Primary Examiner—Jerome D. Goldberg
(74) Attorney, Agent, or Firm—Peter C. Richardson; Paul H. Ginsburg; Raymond M. Speer

(57) ABSTRACT

Known bisamidine compounds are newly discovered to possess DNA methyltransferase inhibiting properties, making them useful for preparing pharmaceutical compositions useful as antiproliferative agents for treating a neoplastic or a non-neoplastic disease characterized by abnormally rapid proliferation of tissue involved in said disease; wherein said bisamidines comprise a compound of Formula (5.0.0):

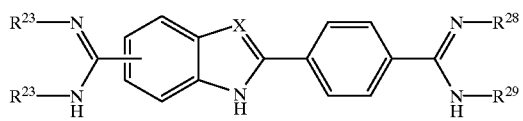

(5.0.0)

and a pharmaceutically acceptable salt thereof, wherein:

—X is —C($R^{34}$)—; or —N—;

—$R^{23}$, $R^{24}$, $R^{28}$ and $R^{29}$ are each independently —H; or —$CH_2$— where $R^{23}$ and $R^{24}$ and $R^{28}$ and $R^{29}$ are taken together with the nitrogen atoms to which they are attached, to form an imidazolinyl group; and —$R^{34}$ is —H; or —$CH_3$. A preferred species of Formula (5.0.0) is the following:

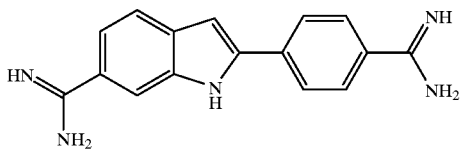

2-(4-Carbamimidoyl-phenyl)-1H-indole-6-carboxamidine.

4 Claims, No Drawings

BISAMIDINE COMPOUNDS AS ANTIPROLIFERATIVE AGENTS

REFERENCE TO COPENDING APPLICATIONS

Reference is made to copending U.S. application Ser. No. PCT/IB98/01710 filed Oct. 26, 1998; which is a §371 application based on U.S. provisional application Ser. No. 60/064,198 filed Nov. 4, 1997, and now abandoned. This application discloses antineoplastic and antiproliferative agents which are indazole bioisostere replacement compounds. However, none of the active agents disclosed therein is the same as, or would suggest, the compounds used as antiproliferative agents in the methods of treatment of the present invention.

BACKGROUND OF THE INVENTION

The present invention is concerned with a new use for certain known bisamidine compounds. It has been discovered that said known compounds possess biological activity as inhibitors of the DNA methyltransferase enzyme and consequently are useful in the treatment of diseases and conditions which involve unregulated differentiation of cells and cellular proceses. The DNA methyltransferase enzyme (EC 2.1.1.37) catalyzes the covalent methylation of the DNA base cytosine at the C5 position of that base. This modification of the base cytosine in a DNA molecule has been shown to play a vital role in the transcriptional inactivation, i.e., silencing of the chromatin as well as in the development and differentiation of cells. The resulting unregulated differentiation of cells and cellular processes is found to be a contributing factor in the development via transformation, and growth of particular cancers and malignancies. The compounds used in the methods of treatment of the present invention hinder the occurrence of the just-described biochemical process and constrain its pathogenic sequelae. As a result, the known compounds of Formula (5.0.0) are useful as chemopreventative and chemotherapeutic agents in the methods of treating cancers, proliferative diseases such as psoriasis, and hyperplasia, which comprise the present invention.

DESCRIPTION OF THE STATE OF THE ART

The DNA methyltransferase enzyme (EC 2.1.1.37), which has been identified as a single gene product of 190 Kd, catalyzes the cofactor S-adenosylmethionine (SAM) dependent methylation of the cytosine base at the C5 carbon of the pyrimidine base. See, e.g., T. H. Bestor and V. M. Ingram, *Proc. Nat Acad. Sci.*, 80:5559–5563 (1983). This DNA modification has been shown to play a vital role in the transcriptional inactivation, i.e., silencing of the chromatin, as well as in the development and differentiation of cells, as described in more detail in E. Li, T. H. Bestor and R. Jaenisch, *Cell,* 69:915–926 (1992).

It is important to point out that aberrant changes in DNA methylation patterns as well as DNA methyltransferase activity itself have been implicated in the progression of cancer. There are two proposed mechanisms by which DNA methyltransferase has been correlated with this progression. (A) The first proposed mechanism is the hypermethylation/ hypomethylation of key cell cycle regulatory genes and oncogenes including P16, P15, c-myc and P53. See, e.g., M. Schroeder and Mass, M. J., *Biochem.& Biophys. Res. Comm.,* 235:403406 (1997). (B) The second proposed mechanism is the low frequency DNA methyltransferase mediated deamination of the cytosine base causing a cytosine to thymine point mutation in the DNA sequence. See, e.g., J.-C. Shen, W. M. Rideout III and P. A. Jones, *Cell,* 71:1073–1080 (1992).

Further work in the art also supports the correlation between DNA methyltransferase activity and the transformation and progression of colon cells to malignant carcinomas in min/APC (–/–) knock-out mice, as described in more detail in P. W. Laird, L. Jackson-Grusby, A. Fazell, S. L. Dickinson, W. E. Jung,. E. Li, R. A. Wienberg and R. Jaenisch, *Cell,* 81:197–205 (1995).

SUMMARY OF THE INVENTION

The present invention relates to a pharmaceutical composition for use as an antiproliferative agent, comprising a therapeutically effective amount of a bisamidine compound of Formula (5.0.0) as described further below, together with a pharmaceutically acceptable carrier for said compound. The present invention relates as well to a corresponding method of treating a neoplastic or a non-neoplastic disease characterized by abnormally rapid proliferation of tissue involved in said disease, comprising administering to a patient in need of such treatment a therapeutically effective amount of a compound of Formula (5.0.0) as described further below. Said patient is a mammal, including especially a human. Said neoplastic disease includes but is not limited to melanoma, colon cancer; bladder cancer, non-small cell lung cancer, gliomas, head and neck squamous cell carcinoma, breast cancer, prostate cancer, renal cancer, and nasopharyngeal carcinoma. Said non-neoplastic disease includes but is not limited to psoriasis, *Pneumocystis carinii* infection, and restenosis.

The present invention further relates to a pharmaceutical composition for use as a DNA methyltransferase inhibiting agent, comprising a therapeutically effective amount of a bisamidine compound of Formula (5.0.0) as described further below, together with a pharmaceutically acceptable carrier for said compound. The present invention relates as well to a corresponding method of treating a neoplastic or a non-neoplastic disease characterized by abnormally rapid proliferation of tissue involved in said disease which is mediated by or associated with abnormally increased levels of DNA methylation, comprising administering to a patient in need of such treatment a therapeutically effective amount of a compound of Formula (5.0.0) as described further below. Said patient is a mammal, including especially a human. Said neoplastic disease includes but is not limited to melanoma, colon cancer; bladder cancer, non-small cell lung cancer, gliomas, head and neck squamous cell carcinoma, breast cancer, prostate cancer, renal cancer, and nasopharyngeal carcinoma. Said non-neoplastic disease includes but is not limited to psoriasis, *Pneumocystis carinii* infection, and restenosis.

The antineoplastic and antiproliferative agents used in the methods of treatment of the present invention are useful as well in the therapy of psoriasis, a non-neoplastic disease of the skin characterized by abnormally rapid proliferation of epidermal cells, as well as for the beneficial treatment of *Pneumocystis carinii*. Therapeutic agents used in the methods of treatment of the present invention are further useful in the treatment of proliferative diseases such as restenosis, in addition to cancer and psoriasis.

The present invention relates to the use of certain bisamidine compounds as antiproliferative agents, wherein said bisamidine comprises a compound of Formula (5.0.0):

(5.0.0)

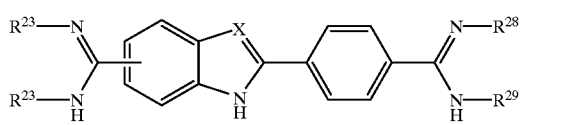

and a pharmaceutically acceptable salt thereof, wherein:
- —X is —C($R^{34}$)—; or —N—;
- —$R^{23}$, $R^{24}$, $R^{28}$ and $R^{29}$ are each independently —H; or —CH$_2$— where $R^{23}$ and $R^{24}$ and
- $R^{28}$ and $R^{29}$ are taken together with the nitrogen atoms to which they are attached, to form an imidazolinyl group; and
- —$R^{34}$ is —H; or —CH$_3$.

DETAILED DESCRIPTION OF THE INVENTION

The present invention is concerned with certain known bisamidines which have been discovered to be newly useful as antiproliferative agents. Said bisamidines comprise a compound of Formula (5.0.0):

(5.0.0)

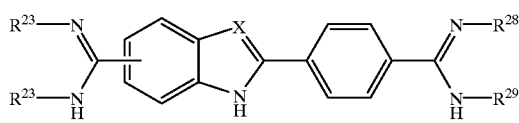

and a pharmaceutically acceptable salt thereof.

The X moiety of the compounds of Formula (5.0.0) has the meaning —C($R^{34}$)— or —N—. Accordingly, there results an indolyl-2-phenyl moiety with a 3-position substituent $R^{34}$ as the nucleus of the compounds of Formula (5.0.0) when X has the meaning —C($R^{34}$)—; and a benzimidazolinyl-2-phenyl moiety as the nucleus of the compounds of Formula (5.0.0) when X has the meaning —N—. These basic nuclei may be represented by partial Formulas (5.1.0) and (5.2.0) as follows:

(5.1.0)

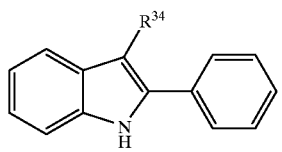

(5.2.0)

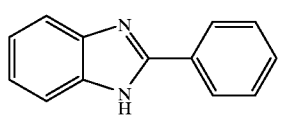

Of the two above-depicted nuclei, the indolyl-2-phenyl moiety of Formula (5.1.0) is preferred.

The 1-position nitrogen atom of either the indolyl-2-phenyl or benzimidazolinyl-2-phenyl nucleus has only a hydrogen attached thereto, i.e., there is no substitution of said nitrogen atom.

Where $R^{23}$, $R^{24}$, $R^{28}$ and $R^{29}$ all have the meaning —H, the compounds of Formula (5.0.0) are characterized by having a carbamimidoyl group attached to either the indolyl or benzimidazolinyl component of the basic nucleus, as well as to the phenyl component of said nucleus. These carbamimidoyl groups may be attached only to specific carbon atoms of said components. Particularly, the carbamimidoyl group must be attached at the 4-position of the phenyl component of the nucleus, and must be attached at either the 5- or 6-position of the indolyl-2-phenyl or benzimidazolinyl-2-phenyl nucleus. The following structural formulas are illustrative of the possible configurations included within the scope of the compounds of Formula (5.0.0), shown by partial Formulas (5.3.1) through (5.3.4), inclusive:

(5.3.1)

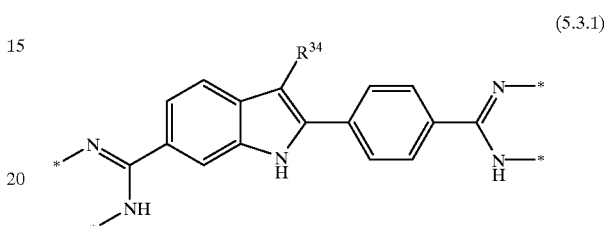

(5.3.2)

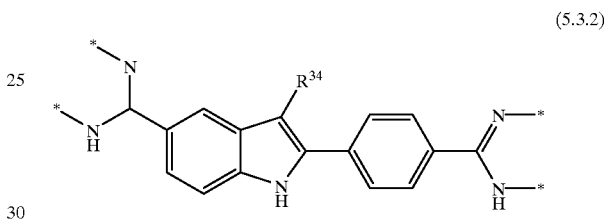

(5.3.3)

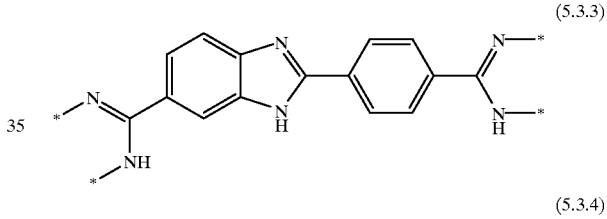

(5.3.4)

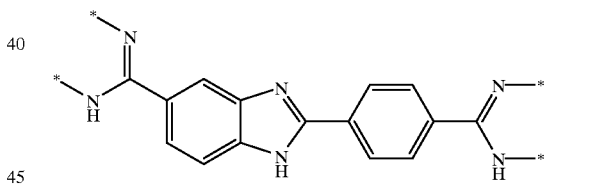

where the symbol "*" indicates the points of attachment of the substituents $R^{23}$, $R^{24}$, $R^{28}$ and $R^{29}$, which are not shown in order to simplify the illustration.

Of the above-depicted configurations, those of partial Formulas (5.3.1) and (5.3.3) are preferred, and that of partial Formula (5.3.1) is most preferred in compounds useful in the methods of treatment of the present invention.

The substituents on the carbamimidoyl groups illustrated in partial Formulas (5.3.1) through (5.3.4) above are designated $R^{23}$, $R^{24}$, $R^{28}$ and $R^{29}$ and in one embodiment they are each hydrogen. In this embodiment of compounds useful in the methods of treatment of the present invention, accordingly, the carbamimidoyl substituents on the indolyl-2-phenyl and benzimidazolinyl-2-phenyl nuclei all have the configuration of the group illustrated by partial Formula (5.4.1):

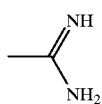

(5.4.1)

In another embodiment of the compounds of Formula (5.0.0) useful in the methods of treatment of the present invention, $R^{23}$ and $R^{24}$ are taken together, and $R^{28}$ and $R^{29}$ are taken together, with the nitrogen atoms to which they are attached, to form an imidazolinyl group This embodiment may be illustrated by the following partial Formula (5.5.1):

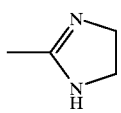

(5.5.1)

$R^{34}$ is the substituent which is present on the 3-position carbon atom of the indolyl-2-phenyl nucleus of partial Formula (5.1.0), or on the 3-position nitrogen atom of the benzimidazolinyl-2-phenyl nucleus of partial Formula (5.2.0). $R^{34}$ has the meaning of —H or —CH$_3$, and is essentially the only substituent which appears on the compounds of Formula (5.0.0).

The above description contains an indication of subgeneric areas within the scope of the compounds of Formula (5.0.0) which are preferred for use in the methods of treatment of the present invention. There are also specific embodiments within the scope of the compounds of Formula (5.0.0) which are preferred for use in the methods of treatment of the present invention. These specific embodiments include but are not limited to those illustrated in the following Formulas (6.0.1) through (6.0.6) inclusive:

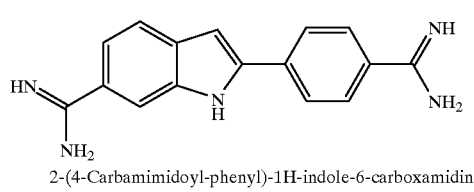

(6.0.1)

2-(4-Carbamimidoyl-phenyl)-1H-indole-6-carboxamidine

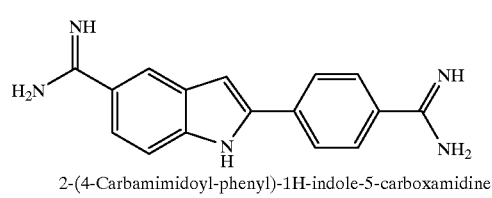

(6.0.2)

2-(4-Carbamimidoyl-phenyl)-1H-indole-5-carboxamidine

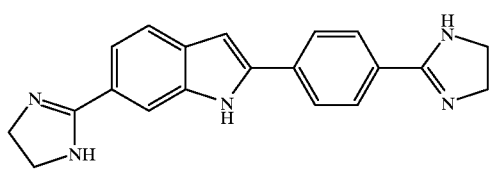

(6.0.3)

6-(4,5-Dihydro-1H-imidazol-2-yl)-2-[4-(4,5-dihydro-1H-imidazol-2-yl)-phenyl]-1H-indole

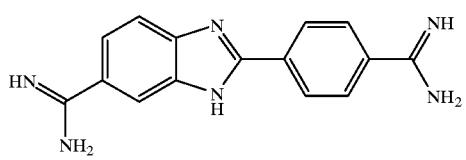

(6.0.4)

2-(4-Carbamimidoyl-phenyl)-3H-benzoimidazole-6-carboxamidine

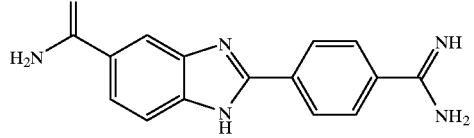

(6.0.5)

2-(4-Carbamimidoyl-phenyl)-3H-benzoimidazole-5-carboxamidine

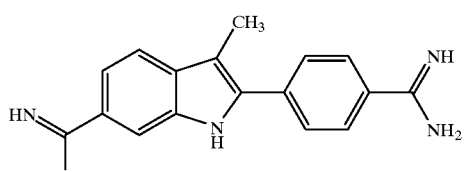

(6.0.6)

2-(4-Carbamimidoyl-phenyl)-3-methyl-1H-indole-6-carboxamidine

The above-described compounds of Formula (5.0.0) may be utilized in the form of acids, esters, or other chemical classes of compounds to which the compounds described belong. It is also within the scope of the present invention to utilize those compounds in the form of pharmaceutically acceptable salts derived from various organic and inorganic acids and bases in accordance with procedures well known in the art. Such well-known pharmaceutically acceptable salts include, but are not limited to acetate, adipate, alginate, aspartate, benzoate, benzenesulfonate, besylate, bisulfate, butyrate, citrate, camphorate, camphorsulfonate, cyclopentanepropionate, digluconate, dodecysulfate, ethanesulfonate, fumarate, glucoheptanoate, gluconate, glycerophosphate, hemisuccinate, hemisulfate, heptanoate, hexanoate, hippurate, hydrochloride, hydrobromide, hydroiodide, 2-hydroxyethanesulfonate, isethionate, lactate, lactobionate, maleate, mandelate, methanesulfonate, 2-naphthalenesulfonate, nicotinate, nitrate, oxalate, oleate, pamoate, pectinate, persulfate, 3-phenylpropionate, phosphonate, picrate, pivalate, propionate, salicylate, sodium phosphate, stearate, succinate, sulfate, sulfosalicylate, tartrate, thiocyanate, thiomalate, tosylate, and undecanoate.

Base salts of the compounds of the present invention include, but are not limited to ammonium salts; alkali metal salts such as sodium and potassium; alkaline earth metal salts such as calcium and magnesium; salts with organic bases such as dicyclohexylamine, meglumine, N-methyl-D-glucamine, tris-(hydroxymethyl)-methylamine (tromethamine), and salts with amino acids such as arginine, lysine, etc. Compounds of the present invention which comprise basic nitrogen-containing groups may be quaternized with such agents as ($C_1$–$C_4$) alkyl halides, e.g., methyl, ethyl, iso-propyl and tert-butyl chlorides, bromides and iodides; di($C_1$–$C_4$) alkyl sulfate, e.g., dimethyl, diethyl and diamyl sulfates; ($C_{10}$–$C_{18}$) alkyl halides, e.g., decyl, dodecyl, lauryl, myristyl and and stearyl chlorides, bromides and iodides; and aryl-($C_1$–$C_4$) alkyl halides, e.g., benzyl chloride and phenethyl bromide. Such salts permit the preparation of both water-soluble and oil-soluble compounds of the present invention.

Among the above-recited pharmaceutical salts those which are preferred include, but are not limited to acetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate, and tromethamine.

Multiple salts forms are included within the scope of the present invention where a compound of the present invention contains more than one group capable of forming such pharmaceutically acceptable salts. Examples of typical multiple salt forms include, but are not limited to bitartrate, diacetate, difumarate, dimeglumine, diphosphate, disodium, and trihydrochloride.

The pharmaceutical compositions of the present invention comprise any one or more of the above-described antiproliferative compounds of the present invention, or a pharmaceutically acceptable salt thereof as also above-described, together with a pharmaceutically acceptable carrier in accordance with the properties and expected performance of such carriers which are well-known in the pertinent art.

The term "carrier" as used herein includes acceptable diluents, excipient, adjuvants and vehicles. Pharmaceutically acceptable carriers that may be used in the pharmaceutical compositions of this invention include but are not limited to, ion exchange compositions; alumina; aluminum stearate; lecithin; serum proteins, e.g., human serum albumin; phosphates; glycine; sorbic acid; potassium sorbate; partial glyceride mixtures of saturated vegetable fatty acids; water; salts or electrolytes, e.g., prolamine sulfate, disodium hydrogen phosphate, potassium hydrogen phosphate, sodium chloride, and zinc salts; colloidal silica; magnesium trisilicate; polyvinyl pyrrolidone; cellulose-based substances; e.g., sodium carboxymethylcellulose; polyethylene glycol; polyacrylates; waxes; polyethylene-polyoxypropylene-block polymers; and wool fat.

More particularly, the diluents, excipient, adjuvants and vehicles used in the pharmaceutical compositions of the present invention comprise members selected from the groups consisting essentially of the following: acidifying and alkalizing agents added to obtain a desired or predetermined pH comprise acidifying agents, e.g., acetic acid, glacial acetic acid, malic acid, and propionic acid, and alkalizing agents, e.g., edetol, potassium carbonate, potassium hydroxide, sodium borate, sodium carbonate, and sodium hydroxide; aerosol propellants required where the pharmaceutical composition is to be delivered as an aerosol under significant pressure, e.g., acceptable halogenated hydrocarbons; nitrogen; or a volatile hydrocarbon such as butane, propane, isobutane or mixtures thereof; antimicrobial agents including antibacterial, antifungal and antiprotozoal agents added where the pharmaceutical composition is topically applied, e.g., antimicrobial agents such as benzyl alcohol, chlorobutanol, phenylethyl alcohol, phenylmercuric acetate, potassium sorbate, and sorbic acid, and antifungal agents such as benzoic acid, butylparaben, ethylparaben, methylparaben, propylparaben, and sodium benzoate; antimicrobial preservatives added to the pharmaceutical compositions in order to protect them against the growth of potentially harmful microorganisms, e.g., alkyl esters of p-hydroxybenzoic acid, propionate salts, phenoxyethanol, methylparaben sodium, propylparaben sodium, sodium dehydroacetate, benzalkonium chloride, benzethonium chloride, and benzyl alcohol; antioxidants added to protect all of the ingredients of the pharmaceutical composition from damage or degradation by oxidizing agents present in the composition itself or the use environment, e.g., anoxomer, ascorbyl palmitate, butylated hydroxyanisole, butylated hydroxytoluene, hypophosphorous acid, potassium metabisulfite, propyl octyl and dodecyl gallate, sodium metabisulfite, sulfur dioxide, and tocopherols; buffering agents used to maintain a desired pH of a composition once established, e.g., calcium acetate, potassium metaphosphate, potassium phosphate monobasic, and tartaric acid; and chelating agents used to help maintain the ionic strength of the pharmaceutical composition and bind to and effectively remove destructive compounds and metals, e.g., edetate dipotassium, edetate disodium, and edetic acid.

Dermatologically active agents are added to the pharmaceutical compositions of the present invention to be applied topically, e.g., wound healing agents such as peptide derivatives, yeast, panthenol, hexylresorcinol, phenol, tetracycline hydrochloride, lamin and kinetin, glucocorticosteroids for treating inflammation, e.g., hydrocortisone, dexamethasone, betamethasone, triamcinolone, fluocinolone and methylprednisolone, retinoids for treating acne, psoriasis, cutaneous aging, and skin cancer, e.g., retinol, tretinoin, isotretinoin, etretinate, acitretin, and arotinoid, immunosuppressive agents for treating inflammation, e.g., dapsone and sulfasalazine; mild antibacterial agents, e.g., resorcinol, salicylic acid, benzoyl peroxide, erythromycin-benzoyl peroxide, erythromycin, clindamycin, and mupirocin, antifungal agents, e.g., griseofulvin, azoles such as miconazole, econazole, itraconazole, fluconazole, and ketoconazole, and allylamines such as naftifine and terfinafine, antiviral agents, e.g., acyclovir, famciclovir, and valacyclovir, antihistamines, e.g., diphenhydramine, terfenadine, astemizole, loratadine, cetirizine, acrivastine, and temelastine, topical anesthetics, e.g., benzocaine, lidocaine, dibucaine, and pramoxine hydrochloride, topical analgesics, e.g., methyl salicylate, camphor, menthol, and resorcinol; topical antiseptics for preventing infection, e.g., benzalkonium chloride and povidone-iodine; vitamins and derivatives thereof such as tocopherol, tocopherol acetate, retinoic acid and retinol.

Further examples of diluents, excipient, adjuvants and vehicles used in the pharmaceutical compositions of the present invention comprise members selected from the groups consisting essentially of the following: dispersing and suspending agents, e.g., poligeenan, povidone, and silicon dioxide; emollients, e.g., hydrocarbon oils and waxes, triglyceride esters, acetylated monoglycerides, methyl and other alkyl esters of $C_{10}$–$C_{20}$ fatty acids, $C_{10}$–$C_{20}$ fatty acids, $C_{10}$–$C_{20}$ fatty alcohols, lanolin and derivatives, polyhydric alcohol esters such as polyethylene glycol (200–600), polyoxyethylene sorbitan fatty acid esters, wax esters, phospholipids, and sterols; emulsifying agents used for preparing oil-in-water emulsions; excipients, e.g., laurocapram and polyethylene glycol monomethyl ether; humectants, e.g., sorbitol, glycerin and hyaluronic acid; ointment bases, e.g., petrolatum, polyethylene glycol, lanolin, and poloxamer; penetration enhancers, e.g., dimethyl isosorbide, diethyl-glycol-monoethylether, 1-dodecylazacycloheptan-2-one, and dimethylsulfoxide (DMSO); preservatives, e.g., benzalkonium chloride, benzethonium chloride, alkyl esters of p-hydroxybenzoic acid, hydantoin derivatives, cetylpyridinium chloride, propylparaben, quaternary ammonium compounds such as potassium benzoate, and thimerosal; sequestering agents comprising cyclodextrins; solvents, e.g., acetone, alcohol, amylene hydrate, butyl alcohol, corn oil, cottonseed oil, ethyl acetate, glycerin, hexylene glycol, isopropyl alcohol, isostearyl alcohol, methyl alcohol, methylene chloride, mineral oil, peanut oil, phosphoric acid, polyethylene glycol, polyoxypropylene 15 stearyl ether, propylene glycol, propylene glycol diacetate, sesame oil, and purified water; stabilizers, e.g., calcium saccharate and thymol; surfactants, e.g., lapyrium chloride; laureth 4, i.e., α-dodecyl-ω-hydroxy-poly(oxy-1,2-ethanediyl) or polyethylene glycol monododecyl ether.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant, such as Rh, HCIX or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added. Alternatively, the pharmaceutical compositions of this invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation, as described above, or in a suitable enema formulation. Topically active transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate, cetyl esters wax, cetearyl alcohol, 2-octyldodecanol, benzyl alcohol and water.

For ophthalmic use, the pharmaceutical compositions may be formulated as micronized suspension in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, hydrofluorocarbons, and/or other conventional solubilizing or dispersing agents.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

The dosage and dose rate of a compound of Formula (5.0.0) effective for preventing, inhibiting, suppressing or reducing the unregulated differentiation of cells and cellular processes, and consequent or associated pathogenic processes mediated by the DNA methyl transferase enzyme will depend on a variety of factors, such as the chemical nature and biological activity of the inhibitor, the size of the patient, the goal of the treatment, the nature of the pathology to be treated, the specific pharmaceutical composition used, and the observations and conclusions of the treating physician.

For example, where the dosage form is oral, e.g., a tablet or capsule, suitable dosage levels of the compounds of Formula (5.0.0) will be between about 1.0 $\mu$g and about 10.0 mg/kg body weight per day, preferably between about 5.0 $\mu$g and about 5.0 mg/kg body weight per day, more preferably between about 10.0 $\mu$g and about 1.0 mg/kg of body weight per day, and most preferably between about 20.0 $\mu$g and about 0.5 mg/kg of body weight per day of the active ingredient.

Where the dosage form is topically administered by means of an ointment, suitable dosage levels of a compound of Formula (5.0.0) will be between about 0.1 $\mu$g and about 1.0 mg/kg body weight per day, preferably between about 0.5 $\mu$g and about 0.5 mg/kg body weight per day, more preferably between about 1.0 $\mu$g and about 0.1 mg/kg of body weight per day, and most preferably between about 2.0 $\mu$g and about 0.05 mg/kg of body weight per day of the active ingredient.

Using representative body weights of 10 kg and 100 kg in order to illustrate the range of daily topical dosages which might be used as described above, suitable dosage levels of the compounds of Formula (5.0.0) will be between about 1.0–10.0 $\mu$g and 10.0–100.0 mg per day, preferably between about 5.0–50.0 $\mu$g and 5.0–50.0 mg per day, more preferably between about 10.0–100.0 $\mu$g and 1.0–10.0 mg per day, and most preferably between about 20.0–200.0 µg and about 0.5–5.0 mg per day of the active ingredient comprising a compound of Formula (5.0.0). These ranges of dosage amounts represent total dosage amounts of the active ingredient per day for a given patient. The number of times per day that a dose is administered will depend upon such pharmacological and pharmacokinetic factors as the half-life of the active ingredient, which reflects its rate of catabolism and clearance, as well as the minimal and optimal blood plasma or other body fluid levels of said active ingredient attained in the patient which are required for therapeutic efficacy Numerous other factors must also be considered in deciding upon the number of doses per day and the amount of active ingredient per dose which will be administered. Not the least important of such other factors is the individual response of the patient being treated. Thus, for example, where the active ingredient is used to treat or prevent psoriasis, and is administered topically via ointment with from one to four applications, will be administered each day, each dose, i.e., ointment application containing from about 50.0 µg to about 10.0 mg of active ingredient.

Included within the scope of the present invention are embodiments comprising compositions which contain, in addition to a compound of Formula (5.0.0) as active ingredient, additional therapeutic agent active ingredients selected from the group consisting essentially of anti-inflammatory corticosteroids; non-steroidal anti-inflammatories; immunosuppressants; immunostimulants; antimetabolites; antipsoriatics, anti-cancer agents, and antidiabetics. Specific compounds within each of these classes may be selected from those listed under the appropriate headings in *Comprehensive Medicinal Chemistry*, Pergamon Press, Oxford, England, pp. 970–986 (1990); and *Goodman and Gilman's The Pharmacological Basis of Therapeutics*, 9th ed., Hardman, J. G. and Limbird, L. E., eds., McGraw-Hill, 1996, the disclosure of which are incorporated herein by reference in their entireties. Especially preferred active ingredients to be included for use in combination with the compounds of Formula (5.0.0) are anti-inflammatory compounds such as theophylline, sulfasalazine and aminosalicylates; immunosuppressants such as cyclosporin, FK-506, and rapamycin; antimetabolites such as cyclophosphamide and methotrexate; and immunomodulators such as the interferons.

As has already been pointed out, the present invention relates to a method of treating a neoplastic or a non-neoplastic disease characterized by abnormally rapid proliferation of tissue involved in said disease, comprising administering to a patient in need of such treatment a therapeutically effective amount of a compound of Formula (5.0.0) as above described. Said patient is a mammal, including especially a human. Said neoplastic disease includes but is not limited to melanoma, colon cancer; bladder cancer, non-small cell lung cancer, gliomas, head and neck squamous cell carcinoma, breast cancer, renal cancer, and nasopharyngeal carcinoma. Said non-neoplastic disease includes but is not limited to psoriasis, *Pneumocystis carinii* infection, and restenosis.

The present invention further relates to a pharmaceutical composition for use as a DNA methyltransferase inhibiting agent, comprising a therapeutically effective amount of a compound of Formula (5.0.0) as above described, together with a pharmaceutically acceptable carrier for said compound. The present invention relates as well to a corresponding method of treating a neoplastic or a non-neoplastic disease characterized by abnormally rapid proliferation of tissue involved in said disease which is mediated by or associated with abnormally increased levels of DNA methylation, comprising administering to a patient in need of such treatment a therapeutically effective amount of a compound of Formula (5.0.0) as above described. Said patient is a mammal, including especially a human. Said patient is a mammal, including especially a human. Said neoplastic disease includes but is not limited to melanoma, colon cancer; bladder cancer, non-small cell lung cancer, gliomas, head and neck squamous cell carcinoma, breast cancer, prostate cancer, renal cancer, and nasopharyngeal carcinoma. Said non-neoplastic disease includes but is not limited to psoriasis, *Pneumocystis carinii* infection, and restenosis.

Antineoplastic and antiproliferative agents of the present invention may also be used in the therapy of psoriasis, a non-neoplastic disease of the skin characterized by abnormally rapid proliferation of epidermal cells, as well as for the beneficial treatment of *Pneumocystis carinii*. Therapeutic agents of the present invention are useful in the treatment of proliferative diseases such as restenosis, in addition to cancer and psoriasis.

The above-described methods of treatment of the present invention may employ the compounds of Formula (5.0.0) in the form of monotherapy, but said methods may also be used in the form of multiple therapy in which one or more compounds of Formula (5.0.0) are co-administered in combination with a known anti-inflammatory, immunomodulating, immunostimulating or immunosuppressive agent. The terms "co-administered" or "co-administration" as used herein are intended to mean therapeutic utilization of one or more compounds of Formula (5.0.0) in combination with one or more additional therapeutic agents, including but not limited to, administration of the combination of therapeutic active agents in a single dosage form or in multiple dosage forms representing the same or different routes of administration, said multiple dosage forms being administered at substantially the same time or at different times.

Subsequent to synthesis of any of the above-recited preferred species falling within the scope of Formula (5.0.0), the biological activities relating to the DNA methyltransferase inhibitory specificities of said compounds may be determined using one or more of the numerous in vitro and in vivo assays which have been described heretofore in the technical literature pertinent to the art. For example, some of the now very-well established assay methods and models concern measurement of DNA methyltransferase inhibitory activity by determining the concentration of a test candidate inhibitor required to block the binding of DNA methyltransferase contained in a cell lysate to a substrate for said enzyme consisting of poly(dl-dC):(dl-dC). The methyl donor S-adenosyl-L-[methyl $^3$H] methionine (SAM) is also present. After incubation the methylated poly(dl-dC):(dl-dC) product is collected on a filter such as DEAE-Sephadex, epichlorohydrin crosslinked dextran 2-(diethylamino)ethyl 2-[[2-(diethylamino)ethyl]diethylamino]ethyl ether chloride hydrochloride, and after drying, the amount of said product bound to said filter is determined by scintillation counting.

The compounds of the present invention may be formulated into pharmaceutical compositions that may be administered orally, parenterally, by inhalation (metered dose inhaler, dry powder inhaler or nebulizer), topically, rectally, nasally, intraocularly, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

The preferred species of Formulas (6.0.1) through (6.0.6) recited further above are known compounds whose preparation has been described in the technical literature. Other species of compounds within the scope of Formula (5.0.0) may be prepared in accordance with well-known procedures for carrying out the synthesis of organic compounds. A number of different procedures are available which are fully disclosed in the technical literature and with which the skilled artisan will be familiar. There follows a citation of the technical literature in which may be found a description of how to prepare the species of Formulas (6.0.1) through (6.0.6).

2-(4-Carbamimidoyl-phenyl)-1H-indole-6-carboxamidine:
  Dann et al., *Justus Liebigs Ann. Chem.*; 749: 68–89 (1971). The dihydrochloride salt of this compound is sold by Fluka; catalog no. 32680.

2-(4-Carbamimidoyl-phenyl)-1H-indole-5-carboxamidine:
  Dann et al., *Justus Liebigs Ann. Chem.*; 749: 68–89 (1971).

6-(4,5-Dihydro-1H-imidazol-2-yl)-2-[4-(4,5-dihydro-1H-imidazol-2-yl)-phenyl]-1H-indole:
  Dann et al., *Justus Liebigs Ann. Chem.*; 749: 68–89 (1971).

2-(4-Carbamimidoyl-phenyl)-3H-benzoimidazole-5-carboxamidine:
  Dann et al., *Justus Liebigs Ann. Chem.*, 760: 37 (1972).

2-(4-Carbamimidoyl-phenyl)-3-methyl-1H-indole-6-carboxamidine:
  Dann et al., *Justus Liebigs Ann. Chem.*, 749: 68–89 (1971).

EXEMPLIFICATION OF PREFERRED EMBODIMENTS

There follows a description of assays which may be carried out in order to determine the DNA methyltransferase inhibiting properties of a test compound. Said description is presented for the purpose of aiding the person of ordinary skill in testing compounds of Formula (5.0.0) in order to determine appropriate dosage levels of said compound which should be used in carrying out the methods of treatment of the present invention. The instant specification when used in light of the knowledge and experience of a person of ordinary skill, is deemed to be completely adequate for that purpose. Accordingly, the description which follows is not intended to in any way limit the scope of the present invention, and it should not be used in that way. The claims appended hereto define the intended scope of the present invention.

EXAMPLE 1
DNA Methyltransferase Inhibition Study

Materials: The DNA methyltransferase enzyme used in these studies was prepared from Friend murine erythroleukemia cells. The cofactor S-adenosyl-L-[methyl $^3$H]methionine (SAM) was purchased from Amersham Life Science Products. The substrate poly (dl-dC):(dl-dC) and other reagents were purchased from Sigma Chemicals.

Lysate Preparation: The method of cell lysate preparation utilized in this procedure was essentially the same as that described in Kumar, et al., *Biochemistry*, 31(36): 8648–8653 (1992). The cells were grown in suspension, harvested by centrifugation and lysed by 2×30 second pulses of sonication in 5 pellet volumes of lysis buffer (20 mM TrisHCl, pH 7.4, 400 mM NaCl, 5 mM EDTA, 0.1% Nonidet P-40, 25% glycerol, 1 mM Phenylmethylsulfonyl fluoride (PMSF)). The lysed cells were then extracted with an equal volume of pre-equilibrated DEAE-Sepharose and allowed to incubate on ice for 10 minutes, after which the supernatant was recovered by centrifugation at 6000×g. The supernatant was again cleared at 12,000×g and the lysate was aliquoted and stored at −80° C.

Methyltransferase Reaction: The DNA methyltransferase assay was run in assay buffer containing: 20 nM TrisHCl, pH 7.4, 1 nM EDTA, 10% glycerol, 1 mM DTT, 1 mM PMSF. The cell lysate containing the methyltransferase enzyme was added to a concentration of 5 μg protein per reaction. The substrate poly (dl-dC):(dl-dC) was assayed at about 1.89 μM (0.15 μg/100 μL) and the methyl donor S-adenosyl-L-[methyl $^3$H]methionine (SAM) was assayed at 0.9 μM (0.5 μCi/reaction). The reaction was incubated at 37° C. for 90 minutes and the methylated poly (dl-dC):(dl-dC) product was collected on DEAE filters. After drying, the amount of product bound to the filters could be determined by scintillation counting.

What is claimed is:

1. A method of treating a neoplastic disease sensitive to a compound of Formula (5.0.0) as defined below, and characterized by abnormally rapid proliferation of tissue involved in said disease which is mediated by or associated with abnormally increased levels of DNA methylation, comprising administering to a patient in need of such treatment a therapeutically effective amount of a compound of Formula (5.0.0):

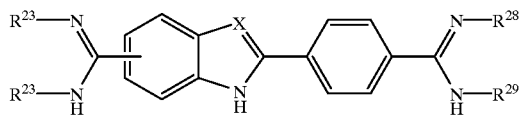

(5.0.0)

or a pharmaceutically acceptable salt thereof, wherein:
  —X is —C(R$^{34}$)—;
  —R$^{23}$, R$^{24}$, R$^{28}$ and R$^{29}$ are each independently —H; or —CH$_2$— where R$^{23}$ and R$^{24}$ and R$^{28}$ and R$^{29}$ are taken together with the nitrogen atoms to which they are attached, to form an imidazolinyl group; and
  —R$^{34}$ is —H; or —CH$_3$.

2. A method according to claim 1 wherein said patient is a human.

3. A method according to claim 1 wherein said neoplastic disease is a member selected from the group consisting of melanoma, colon cancer; bladder cancer, non-small cell lung cancer, gliomas, head and neck squamous cell carcinoma, breast cancer, prostate cancer, renal cancer, and nasopharyngeal carcinoma.

4. A method according to claim 1 wherein said compound of Formula (5.0.0) is a member selected from the group consisting essentially of species of Formula (6.0.1) through (6.0.6) inclusive:

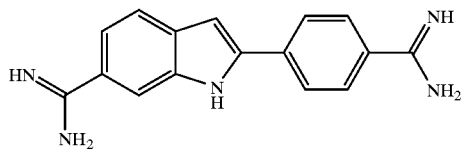

(6.0.1)

2-(4-Carbamimidoyl-phenyl)-1H-indole-6-carboxamidine
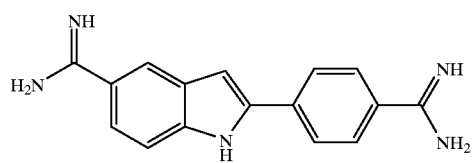
(6.0.2)
2-(4-Carbamimidoyl-phenyl)-1H-indole-5-carboxamidine
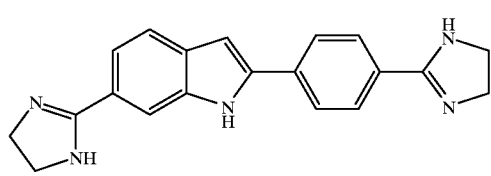
(6.0.3)
6-(4,5-Dihydro-1H-imidazol-2-yl)-2-[4-(4,5-dihydro-1H-imidazol-2-yl)-phenyl]-1H-indole
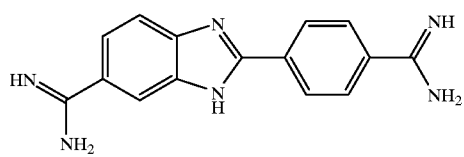
(6.0.4)
2-(4-Carbamimidoyl-phenyl)-3H-benzoimidazole-6-carboxamidine
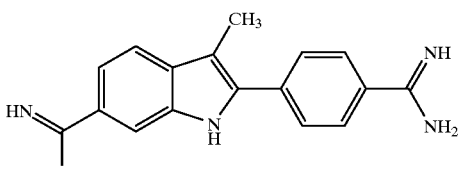
(6.0.5)
2-(4-Carbamimidoyl-phenyl)-3H-benzoimidazole-5-carboxamidine
(6.0.6)
2-(4-Carbamimidoyl-phenyl)-3-methyl-1H-indole-6-carboxamidine.
\* \* \* \* \*